United States Patent
Otto et al.

(10) Patent No.: US 9,200,311 B2
(45) Date of Patent: *Dec. 1, 2015

(54) CIS REACTIVE OXYGEN QUENCHERS INTEGRATED INTO LINKERS

(71) Applicant: Pacific Biosciences of California, Inc., Menlo Park, CA (US)

(72) Inventors: Geoffrey Otto, Brookline, MA (US); Gene Shen, Santa Clara, CA (US); Xiangxu Kong, Union City, CA (US); Robin Emig, Belmont, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 55 days.

This patent is subject to a terminal disclaimer.

(21) Appl. No.: 13/932,749

(22) Filed: Jul. 1, 2013

(65) Prior Publication Data

US 2014/0038178 A1    Feb. 6, 2014

Related U.S. Application Data

(63) Continuation of application No. 12/367,411, filed on Feb. 6, 2009, now Pat. No. 8,501,922.

(60) Provisional application No. 61/026,992, filed on Feb. 7, 2008.

(51) Int. Cl.
*C12Q 1/68* (2006.01)
*C12Q 1/48* (2006.01)
*C07H 21/00* (2006.01)

(52) U.S. Cl.
CPC ........ *C12Q 1/48* (2013.01); *C07H 21/00* (2013.01); *C12Q 1/68* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 6,917,726 B2 | 7/2005 | Levene et al. | |
| 6,936,702 B2 | 8/2005 | Williams et al. | |
| 7,033,764 B2 | 4/2006 | Korlach et al. | |
| 7,220,549 B2 | 5/2007 | Buzby | |
| 7,223,541 B2 | 5/2007 | Fuller et al. | |
| 7,998,717 B2* | 8/2011 | Eid et al. ........... | 435/193 |
| 2002/0042071 A1 | 4/2002 | Williams et al. | |
| 2003/0044781 A1 | 3/2003 | Korlach et al. | |
| 2003/0129642 A1 | 7/2003 | Buechler et al. | |
| 2005/0244827 A1 | 11/2005 | Olsson et al. | |
| 2006/0223076 A1* | 10/2006 | Diwu et al. ........... | 435/6 |
| 2007/0036511 A1 | 2/2007 | Lundquist et al. | |
| 2007/0042398 A1 | 2/2007 | Peng et al. | |
| 2007/0048773 A1 | 3/2007 | Lee et al. | |
| 2007/0117102 A1 | 5/2007 | Buzby | |
| 2007/0128133 A1 | 6/2007 | Eid et al. | |
| 2007/0208169 A1 | 9/2007 | Bodepudi et al. | |
| 2010/0035268 A1 | 2/2010 | Beechem et al. | |

FOREIGN PATENT DOCUMENTS

WO   WO 98/45705 A2   10/1998
WO   WO 99/37717 A1   7/1999

OTHER PUBLICATIONS

Arora, P. S., et al. "Design of Artificial Transcriptional Activators with Rigid Poly-$_L$-proline Linkers" J. Am. Chem. Soc., 2002, vol. 124; pp. 13067-13071.
DiMascio, Paolo, et al., "Carotenoids, Tocopherols, and Thiols as Biological Singlet Molecular Oxygen Quenchers", Biochemical Society Transactions, Dec. 1990, vol. 18, pp. 1054-1056.
Rasnick, et al., Nonblinking and Long-lasting Single-Molecule Fluorescence Imaging, Nature Methods, 3:891-893 (2006).
Stahl, Wilhem, et al., "Biological Activities of Natural and Synthetic Carotenoids: Induction of Gap Junctional Communication and Singlet Oxygen Quenching.", Carcinogenesis, 1997, vol. 18, No. 1; pp. 89-92.
Vierstra R. D., et al., "Effect of Xenon on the Excited States of Phototropic Receptor Flavin in Corn Seedlings", Plant Physiol., 1981, vol. 67; pp. 996-998.
Supplementary European Search Report, EP 09707425.6, May 30, 2014.

* cited by examiner

*Primary Examiner* — Prabha Chunduru
(74) *Attorney, Agent, or Firm* — Morgan, Lewis & Bockius LLP

(57) ABSTRACT

The present invention provides methods and compositions for performing illuminated reactions, particularly sequencing reactions, while mitigating and/or preventing photodamage to reactants that can result from prolonged illumination. In particular, the invention provides methods and compositions for incorporating photoprotective agents into conjugates comprising reporter molecules and nucleoside polyphosphates.

17 Claims, 12 Drawing Sheets

Phospho-peptide coupling: Fmoc-NH-Peptide-Tyr-O-phosphate (or hydroxyproline-O-phosphate) + TTP Iodoacetamide-thiophosphate coupling: Iodoacetamide-peptide-Lys + thiophosphate-pppT

CIS REACTIVE OXYGEN QUENCHERS INTEGRATED INTO LINKERS

CROSS-REFERENCE TO RELATED APPLICATIONS

This application is a continuation of U.S. application Ser. No. 12/367,411 filed on Feb. 6, 2009 which claims priority to U.S. Provisional Application No. 61/026,992, filed Feb. 7, 2008, which is hereby incorporated by reference in its entirety.

STATEMENT REGARDING FEDERALLY SPONSORED RESEARCH

Not applicable.

BACKGROUND OF THE INVENTION

The use of optically detectable labeling groups, and particularly those groups having high quantum yields, e.g., fluorescent or chemiluminescent groups, is ubiquitous throughout the fields of analytical chemistry, biochemistry and biology. In particular, by associating a highly visible signal with a given reaction, one can better monitor that reaction as well as any potential effectors of that reaction. Such analyses are basic tools of life science research in genomics, diagnostics, pharmaceutical research, and related fields.

To date, such analyses have generally been performed under conditions where the amounts of reactants are present far in excess to compensate for any damage caused by the detection system and allow for signal detection with minimal impact on the reactants. For example, analyses based upon fluorescent labeling groups generally require the use of an excitation radiation source directed at the reaction mixture, to excite the fluorescent labeling group, which is then separately detectable. However, one drawback to the use of optically detectable labeling groups is that prolonged exposure of chemical and biochemical reactants to such light sources, alone, or when in the presence of other components, e.g., the fluorescent groups, can damage such reactants. The traditional solution to this drawback is to have the reactants present so far in excess that the number of undamaged reactant molecules outnumbers the damaged reactant molecules, thus minimizing the effects of the photodamage.

A variety of analytical techniques currently being explored deviate from traditional conditions. In particular, many reactions are based upon increasingly smaller amounts of reagents, e.g., in microfluidic or nanofluidic reaction vessels or channels, or in "single molecule" analyses. Such low reactant volumes are increasingly important in many high throughput applications, such as microarrays.

The use of smaller reactant volumes offers challenges to the use of optical detection systems. When smaller reactant volumes are used, damage to reactants, such as from exposure to light sources for fluorescent detection, can become problematic and have a dramatic impact on the operation of a given analysis. This can be particularly detrimental, for example, in real time analyses of reactions that include fluorescent reagents that can expose multiple different reactant components to optical energy. In addition, smaller reactant volumes can lead to limitations in the amount of signal generated upon application of optical energy.

As such, the present invention is directed to methods and compositions that result in increased effective concentrations of reactants and detection molecules in smaller reactant volumes, resulting in an increased signal within the smaller volume. In particular, the present invention provides methods and compositions to prevent or mitigate the adverse effects of photodamage in such reactions.

SUMMARY OF THE INVENTION

In one aspect, the invention provides a compound which includes a nucleoside polyphosphate, a photoprotective agent and a dye.

In another aspect, the invention provides a method for forming a conjugate. Such a method includes the steps of: (i) synthesizing a biopolymer block, where the biopolymer block includes a photoprotective agent, and (ii) conjugating the biopolymer block to a nucleoside polyphosphate.

In still another aspect, the invention provides a device which includes a substrate having an observation region. In a further aspect, the device includes a compound disposed within the observation region. Such a compound can include a nucleoside polyphosphate, a photoprotective agent and a dye.

In yet another aspect, the invention provides a method of performing an illuminated reaction. Such a method includes the step of providing a substrate having a compound disposed thereon. Such a compound can include a nucleoside polyphosphate, a photoprotective agent and a dye. In a further aspect, the method includes the step of illuminating the composition on the substrate with an excitation illumination.

DETAILED DESCRIPTION OF THE INVENTION

Figure 1:
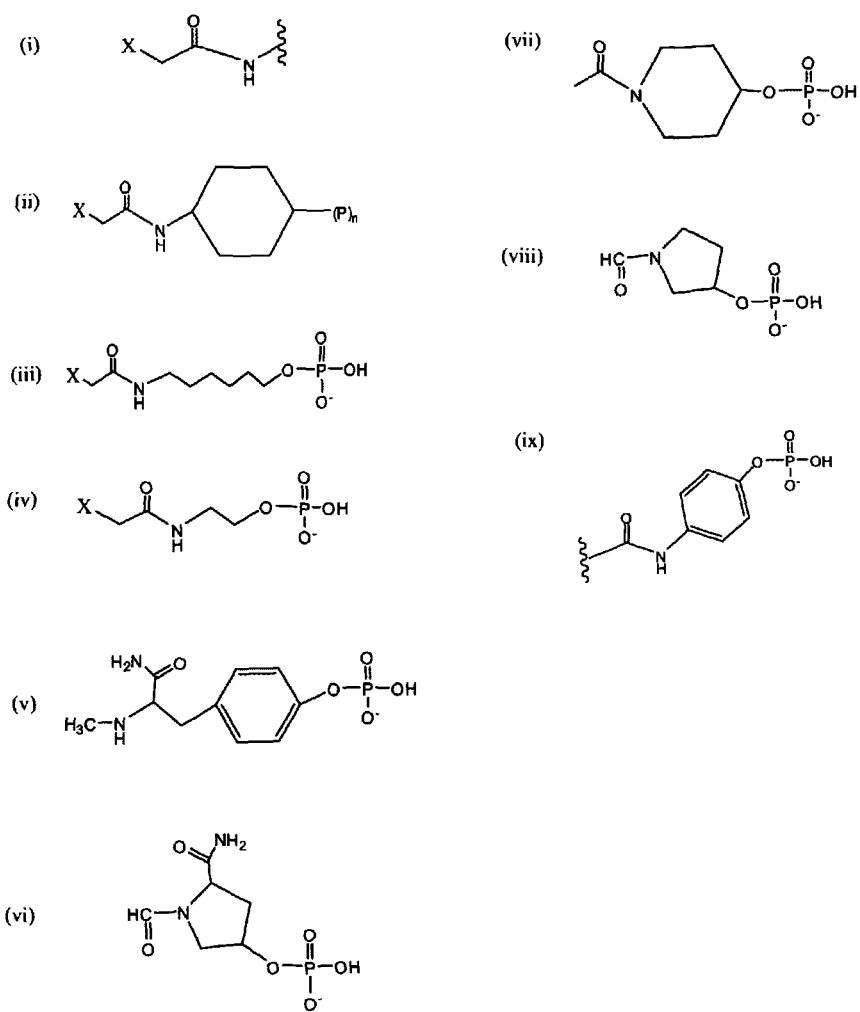
FIG. 1 provides structures of exemplary linking moieties of the invention and molecules from which linking moieties can be derived.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Overview

The present invention is generally directed to compounds, compositions, methods, devices and systems for limiting the effects of photodamage during illuminated reactions, particularly reactions that employ fluorescent or fluorogenic reactants. The term "photodamage" refers generally to any direct or indirect impact of illumination on one or more reagents in a reaction which results in a negative impact upon that reaction. The term "illuminated reactions" as used herein refers to reactions which are exposed to an optical energy source. Typically, such illumination is provided in order to observe the generation and/or consumption of reactants or products that possess a particular optical characteristic indicative of their presence, such as a shift in the absorbance spectrum and/or emission spectrum of the reaction mixture or its components.

In general terms, the invention is directed to the performance of illuminated reaction analyses, where such analyses are illuminated for an amount of time that permits the effective performance of the analysis. In preferred aspects, the invention provides methods and compositions for nucleic acid analysis in which a nucleoside polyphosphate is linked to a fluorescent dye, and wherein the compound further includes, integrated into its structure, a photoprotective agent. As used herein, the term "photoprotective agent" is used interchangeably with the term "photodamage mitigating agent" and generally refers to any agent that can prevent and/or mitigate damages caused by illumination.

In certain exemplary aspects, the dye is linked to the nucleoside polyphosphate by a linker, where the linker itself comprises a photoprotective agent. Such a configuration provides effective mitigation of any resulting photodamage, because the photoprotective agent is in close spatial proximity to the reactants most likely to be damaged by the illumination.

In other mitigation methods, photoprotective agents may generally be provided far in excess of the reactants in order to ensure that the protective effects of the photoprotective agents extend to all reactant molecules in the reaction. However, in small volume reactions, providing such an excess of the photoprotective agent can potentially interfere with the ability of a reaction to proceed to completion. In contrast, the conjugates and compositions of the present invention are particularly useful in small reaction volumes, because incorporating the photoprotective agent into one of the reactants itself removes the need to provide the photoprotective agent in an excess quantity without any decrease in its protective effects.

While the invention is generally applicable to any of a variety of optical assays that require substantial illumination and/or photoactivated conversion or excitation of chemical groups, e.g., fluorophores, it finds particular utility in reactions that utilize very limited concentrations of reactants that might be subject to photodamage. As will be appreciated, in such reagent-limited analyses, any degradation of a critical reagent will dramatically impact the reaction by further limiting the amount of reagent. For example, photodamage can include a photoinduced change in a given reagent that reduces the reactivity of that reagent in the reaction—one example is photobleaching of a fluorescent molecule, which diminishes or removes its ability to act as a signaling molecule. Also included in the term photodamage are other changes that reduce a reactant's usefulness in a reaction, for example, by making the reagent less specific in its activity. Similarly, photodamage includes undesired changes in a reagent that are caused by interaction of that reagent with a product of another photoinduced reaction, e.g., the generation of singlet oxygen during a fluorescence excitation event, which singlet oxygen may damage organic or other reagents, e.g., proteins.

One particularly apt example of reactions that benefit from the invention are single molecule biological analyses, including, inter alia, single molecule nucleic acid sequencing analyses, single molecule enzyme analyses, hybridization assays (e.g., antibody assays), nucleic acid hybridization assays, and the like, where the reagents of primary import are subjected to prolonged illumination from relatively concentrated light sources, (including without limitation lasers and other concentrated light sources, such as mercury, xenon, halogen or other lamps) in an environment where photoconversion/excitation is occurring, with its associated generation of products. Such prolonged illumination can result in photodamage to these reagents and diminish their effectiveness in the desired reaction.

Illuminated Analyses

In a preferred aspect, the invention is directed to mitigating photodamage in illuminated analyses. In general, the terms "illuminated analysis" and "illuminated reaction" are used interchangeably and generally refer to an analytical reaction that is occurring while being illuminated, (e.g., with excitation radiation). Such reactions are generally conducted to evaluate the production, consumption and/or conversion of luminescent, (e.g., fluorescent) reactants and/or products. As used herein, the terms reactant and reagent are used interchangeably. In a preferred embodiment, the illuminated reaction is a sequencing reaction and the photodamage results from an excitation radiation source used to detect nucleotides as they are added to a synthesized nucleic acid strand.

The amount of time an illuminated analysis may be carried out before photodamage so substantially impacts the reactants to render the reaction non-useful, is referred to as the "photodamage threshold period". In terms of the invention, the photodamage threshold period is that period of illuminated analysis during which such photodamage occurs so as to reduce the rate of the subject reaction by at least 10%, 20%, 30%, 40%, 50%, 60%, 70%, 80%, or 90% over the same reaction in the absence of such illumination. It is an object of the invention to increase the photodamage threshold period, thus increasing the amount of time reactions can proceed toward completion with minimal damage to the reactants.

In some contexts, a "photodamaged" reaction may be subject to spurious activity, and thus be more active than desired. In such cases, it will be appreciated that the photodamage threshold period of interest would be characterized by that period of illuminated analysis during which such spurious activity, e.g., as measured by an increase in reaction rate, or an increase in non-specific reaction rate, is no more than 10% over a non-illuminated reaction, no more than 20% over a non-illuminated reaction, no more than 50% over a non-illuminated reaction, and in some cases, no more than 90% over a non-illuminated reaction. In one example (which is not meant to be limiting), where a nucleic acid polymerase, by virtue of a photodamaging event, begins to incorrectly incorporate nucleotides during template directed synthesis, such activity would impact the photodamage threshold period as set forth above. In this case, the compounds and methods of the invention would increase the photodamage threshold period, thus increasing the amount of time the reaction could be illuminated before the above-described spurious activity occurred.

In one example of the negative impact of prolonged illumination on reactions, it has been observed that in template directed synthesis of nucleic acids using fluorescent nucleotide analogs as a substrate, prolonged illumination can result in a substantial degradation in the ability of the polymerase to synthesize the nascent strand of DNA. Damage to or inactivation of polymerase enzymes, template sequences and/or primer sequences can seriously detract from the ability of the polymerase to process longer strands of nucleic acids. Such a reduction in the processivity of an enzyme can have significant effects on many different kinds of reactions, including sequencing reactions. This reduction in processivity of the enzyme, in turn, leads to a reduction in read lengths for sequencing processes that identify sequence constituents based upon their incorporation into the nascent strand. As is appreciated in the art of genetic analysis, the length of contiguous reads of sequence directly impacts the ability to assemble genomic information from segments of genomic DNA. One possible mechanism for this photodamage is that a fluorophore excited by exposure to electromagnetic radiation at an excitation wavelength can transition into a triplet state. This may occur directly, or as a result of multi-photon processes, where an excited fluorophore, when contacted by a photon of a wavelength that is shorter (or bluer) than the nominal excitation wavelength of the fluorophore, transitions to the triplet state. Subsequent relaxation of the triplet state fluorophore can then lead to generation of reactive oxygen species, which can, in turn, damage one or both of the fluorophore or the enzyme processing the fluorophore, e.g., the polymerase. Accordingly, oxygen scavengers and/or reducing agents are needed to prevent the formation of reactive oxygen. Such agents can be included within the conjugates of the invention to alleviate and/or prevent the effects of reactive oxygen species, as well as other species generated during illuminated reaction that can cause photodamage.

Photoprotective Agents

The invention is directed to methods and compounds that reduce the amount of photodamage to one or more reactants during an illuminated reaction. The term "reactant" is used interchangeably with the term "reagent" as used herein.

The compounds of the invention typically include, in addition to a reactant portion and a dye portion, a photoprotective agent integrated into the structure of the compound. In a preferred aspect, compounds of the invention include linkers that comprise photoprotective agents. Photoprotective agents are compositions that yield a reduction in the level of photodamage as compared to such reactions in the absence of such compositions. For ease of discussion, the detrimental impact of the photodamage event, whether resulting from actual damage to a given reagent or from interaction with a damaged reagent, is generally referred to herein as photodamage.

As discussed in further detail herein, the photoprotective agents may be incorporated into compounds of the invention in a variety of different ways, and the compounds of the invention may comprise a wide variety of structures, and as will be appreciated, the compounds of the invention are not limited to the exemplary structures described herein. Unless otherwise noted, the terms "compound of the invention" and "conjugate of the invention" are used interchangeably.

In one embodiment, a conjugate of the invention is a linear molecule which comprises a dye, a nucleoside polyphosphate, and a photoprotective agent. For example, the photoprotective agent may be incorporated into a linker that connects a dye molecule to a nucleoside polyphosphate. In a further non-limiting example, the linear conjugates can comprise a dye, a photoprotective agent, and a nucleoside polyphosphate in any order (i.e., dye-agent-nucleoside, agent-dye-nucleoside, dye-nucleoside-agent, etc.). In still another embodiment, conjugates of the invention have branched structures, in which each of the branches comprise one or more dyes, nucleoside polyphosphates and photoprotective agents. For example, the conjugate may be a tridentate molecule, in which each "arm" of the molecule comprises a photoprotective agent, a dye or a nucleoside polyphosphate, or some combination thereof.

A photoprotective agent may prevent photodamage of one or more reagents, or it may mitigate the impact that a photodamaged reagent may have on another reagent in the reaction of interest. By way of example, an agent that blocks a detrimental interaction between a photodamaged fluorescent compound and a critical enzyme component would still be referred to as a photoprotective agent, regardless of the fact that it did not prevent the initial photodamage to the fluorescent reagent.

In one aspect, the present invention is directed to illuminated reaction mixtures which include one or more agents that function to block or otherwise minimize the pathways that lead to damage due to the creation of reactive oxygen species during an illuminated reaction. In a particularly preferred aspect, the illuminated reaction mixture includes a nucleoside polyphosphate connected to a fluorescent dye by a linker. The linker in such a reaction mixture itself comprises one or more photoprotective agents. Such photoprotective agents can include reducing agents or anti-fade agents that prevent the formation of triplet state fluorophores (also referred to as triplet state quenchers) that can result during the course of an illuminated reaction. Photoprotective agents may also include oxygen scavenging agents, which remove oxygen and reactive oxygen species from the reaction mixture. Such photoprotective agents are able to alleviate and/or prevent photodamage by blocking the damage such species may cause to one or more reactants, particularly conjugates of the invention which include a dye.

In one embodiment, the photoprotective agents incorporated into linkers of the invention include reducing or anti-fade agents which act as triplet state quenchers. A variety of reducing agents or anti-fade agents may be used as triplet state quenchers, including without limitation ascorbic acid, dithiothreitol (DTT), mercaptoethylamine (MEA), β-mercaptoethanol (BME), n-propyl gallate, p-phenylenediamene (PPD), hydroquinone, sodium azide (NaN$_3$), diazobicyclooctane (DABCO), cyclooctatetraene (COT), as well as commercially available anti fade agents, such as Fluoroguard (available from BioRad Laboratories, Inc., Hercules, Calif.), Citifluor antifadants (Citifluor, Ltd., London, UK), ProLong, SlowFade, SlowFade Light (Invitrogen/Molecular Probes, Eugene, Oreg.), and 3-nitrobenzoic acid (NBA). As will be appreciated, in the context of the invention, the foregoing agents may optionally or additionally be included separately from the dye-labeled compounds, e.g., as reaction mixture additives.

In another embodiment, the photoprotective agents incorporated into linkers of the invention include singlet oxygen quenchers. A number of singlet oxygen quenchers may be used to eliminate or reduce reactive oxygen species that can result from illuminated reactions. Such quenchers can include without limitation enzymatic systems, e.g., superoxide dismutase, glucose oxidase/catalase (GO/Cat), oxidase/peroxidase enzyme systems, e.g., glucose oxidase, alcohol oxidases, cholesterol oxidases, lactate oxidases, pyruvate oxidases, xanthine oxidases, and the like, in combination with peroxide depleting enzymes, like horseradish peroxidase (HRP), glutathione peroxidase, or combinations of these with other enzymes, protocatachaute 3,4 dioxygenase (PCD) (a single enzyme oxygen consumer), or thiol based quenchers e.g. ergothioneine, methionine, cysteine, beta-dimethyl cysteine (penicillamine), mercaptopropionylglycine, MESNA, glutathione, dithiothreitol (as noted above for a reducing agent), N-acetyl cysteine and captopril (See, e.g., Biochem Soc. Trans. 1990 December; 18(6): 1054-6), imidazole. Also, biological singlet oxygen quenchers may be employed such as lycopene, α, β, and γ-carotene and their analogs, antheraxanthin, astaxanthin, canthaxanthin, (See, e.g., Carcinogenesis vol. 18 no. 1 pp. 89-92, 1997), neurosporene, rhodopin, bixin, norbixin, zeaxanthin, lutein, bilirubin, biliverdin, and tocopherols (See, e.g., Biochem Soc Trans. 1990 December; 18(6): 1054-6 ref.) as well as polyene dialdehydes (Carcinogenesis vol. 18 no. 1 pp. 89-92, 1997) melatonin, vitamins E (α-tocopheryl succinate and its analogs) and B$_6$ (pyridoxinel and its derivatives). Other chemical oxygen scavengers are also available, e.g., hydrazine (N$_2$H$_4$), sodium sulfite (Na$_2$SO$_3$), hydroxylamine, glutathione, and N-acetylcysteine, histidine, tryptophan, and the like. In addition to the foregoing, in many cases, the amount of singlet oxygen quenchers or scavengers may be reduced or eliminated by physically excluding oxygen from the reaction of interest by, e.g., degassing reagents, perfusion with inert gases, or the like. In addition to the foregoing, as an additional or alternative to the foregoing compounds, anti-oxidants may also be provided in the reaction mixture, including, e.g., Trolox and its analogs U-78715F and WIN62079, a soluble form of vitamin E, having a carboxyl substitution, or in the case of analogs, other substitutions, in place of the vitamin E phytyl side chain, ascorbic acid (or ascorbate), butylated hydroxytoluene (BTH), and the like. Further examples of anti-oxidants that can be included in compositions of the invention are amino acids that are easily oxidized, such as methionine. Such amino acids can be included in linkers of the invention, and one or more of such residues can form part or all of the linker (for example, as a poly-amino acid chain comprising multiple anti-oxidant amino acids). Natural and non-natural amino acids that are easily oxidized would all be encompassed in this embodiment of the invention. In further embodiments, other amino acids may also be included to protect against other radicals that are not necessarily formed directly during an illuminated reaction but may be created in downstream reactions as a result of photodamage that can occur in an illuminated reaction. For example, lysine is beneficial for scrubbing formaldehyde and hydroxide radicals from a system.

Other enzyme systems may be likewise employed in the depletion of oxygen species. In one embodiment, such systems may include an oxidase enzyme, such as glucose oxidase, alcohol oxidases, cholesterol oxidases, lactate oxidases, pyruvate oxidases, xanthine oxidases, and the like, in combination with a peroxidase enzyme, such as Horseradish Peroxidase (HRP). HRP is a widely available peroxidase that readily converts hydrogen peroxide present in solution into water in the presence of an oxidizable substrate, i.e., Amplex Red, O-phenylene diamine (ODP), luminol. Thus, in conjunction with, for example, a glucose oxidase system, (e.g., a glucose oxidase enzyme, glucose, in an oxygen containing system) the enzyme will utilize solution oxygen in converting glucose to D-glucono-1,4-lactone and hydrogen peroxide. The HRP then converts the peroxide to water while oxidizing an electron donor substrate, such as luminol, ODP, or the like.

Without being bound to a particular theory or mechanism of operation, it is believed that at least one cause of photodamage to enzyme activity, particularly in the presence of fluorescent reagents, results from the direct interaction of the enzyme with photodamaged fluorescent reagents. Further, it is believed that this photodamage of the fluorescent reagents (and possibly additional damage to the enzyme) is at least partially mediated by reactive oxygen species that are generated during the relaxation of triplet state fluorophores in the presence of molecular oxygen. One or both of the photodamaged fluorescent reagents and/or reactive oxygen species may be included in the overall detrimental effects of photodamage.

The inclusion of photoprotective agent(s) of the invention generally results in a reduction of photodamage of one or more reactants in a given reaction, as measured in terms of "prevented loss of reactivity", in the system. Using methods known in the art, the amount of prevented loss of reactivity can be of at least 10%, preferably, greater than 20%, and more preferably, greater than about a 50% reduction, and in many cases greater than a 90% and up to and greater than 99% reduction in such photodamage. By way of illustration, and purely for the purpose of example, when referring to reduction in photodamage as a measure of enzyme activity in the presence and absence of the photoprotective agent, if a reaction included a reaction mixture having 100 units of enzyme activity that would, in the absence of a photoprotective agent, and following illuminated analysis, yield a reaction mixture having only 50 units of activity, then a 10% reduction in photodamage would yield a final reaction mixture of 55 units (e.g., 10% of the 50 units otherwise lost, would no longer be lost).

Conjugates of the Invention

As described herein, conjugates of the invention may comprise a wide variety of structures. In one aspect, the conjugates of the invention are linear molecules that include a dye, a nucleoside polyphosphate and a photoprotective agent in some configuration. In another aspect, the conjugates are branched structures that can also include a dye, a nucleoside polyphosphate and a photoprotective agent in some configuration. Although the following exemplary embodiments describe conjugates comprising only a single dye, photoprotective agent and nucleoside polyphosphate, it is noted that conjugates of the invention may contain multiple dye, photodamage, linker and nucleoside polyphosphate moieties.

In an exemplary aspect, the invention provides linear compounds which typically correspond to the general scheme:

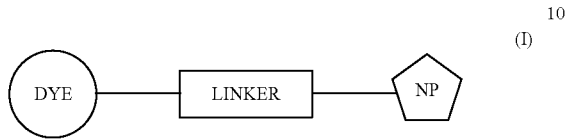

(I)

As used herein, such compounds are also referred to as "conjugates". In structure (I), "DYE" refers generally to reporter molecules that provide a detectable signal, including fluorescent dyes, radioactive atoms, and chemiluminescent groups. In a preferred embodiment, the dye is a fluorescent dye, for example, fluorescein isothiocyanate, Texas red, rhodamine, and the like.

"NP" refers to a nucleoside polyphosphate, which comprises naturally occurring nucleoside triphosphates, nucleoside triphosphate analogs, and nucleoside polyphosphate analogs that include more than three phosphate groups in the chain, e.g., four, five, six or more phosphate groups in the polyphosphate chain. Examples of such polyphosphates have been described in e.g., U.S. Pat. Nos. 6,936,702 and 7,223,541, the full disclosures of which are incorporated herein by reference in their entirety for all purposes, and particularly incorporated without limitation for this aspect of their teachings. Although exemplary embodiments described herein may refer to "nucleoside triphosphates", it will be appreciated that any nucleoside polyphosphate may be utilized in such embodiments.

"LINKER" refers to a moiety which links the dye to the nucleoside polyphosphate. Those of skill in the art will appreciate that a linker can be of any form that is suitable to bind to the dye and to the nucleoside polyphosphate, thereby "linking" the two molecules together. Generally, a linker will be formed from a molecule comprising reactive functional groups which are complementary to the dye and/or the nucleoside polyphosphate, thereby forming the necessary bonds. In a particularly preferred aspect, the linker also comprises a photoprotective agent, such as those described herein. As used herein, the term "linker" and "linking moiety" are used interchangeably.

Alternative configurations to the linear molecule pictured in scheme I are also encompassed by the present invention. For example, a linear conjugate may correspond to the following general configurations:

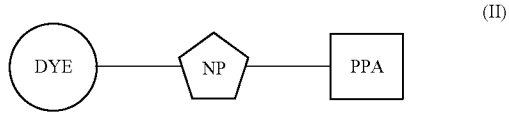

(II)

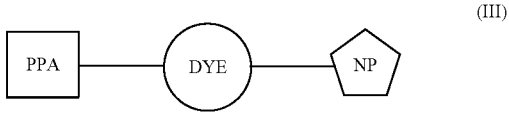

(III)

where "PPA" refers to photoprotective agent. In the above schemes and in the exemplary embodiments discussed further herein, PPA may be directly linked to DYE and/or NP, or indirectly through one or more intervening moieties.

As will be appreciated, conjugates of the invention may comprise branched structures, in which one or more of the "branches" comprises a photoprotective agent, a dye and a nucleoside polyphosphate in a variety of different configurations. In one non-limiting embodiment, the branched conjugate corresponds to the following general scheme:

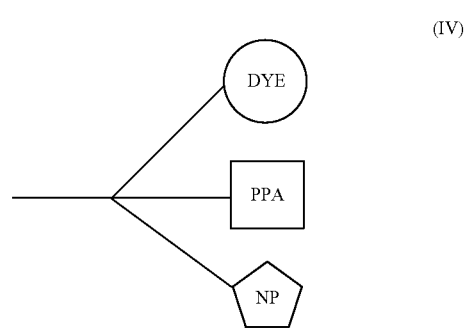

(IV)

wherein the molecule comprises three "branches" or "arms", each of which comprises a dye, a photoprotective agent, or a nucleoside polyphosphate. As will be appreciated, the dye, PPA and NP can be in any configuration among the different branches of the molecule. In addition, a branched conjugate of the invention is not limited to having each of the dye, PPA and NP on a separate branch, and single branches may comprise any combination of the three components.

In another exemplary embodiment, a branched conjugate corresponds to the following general scheme:

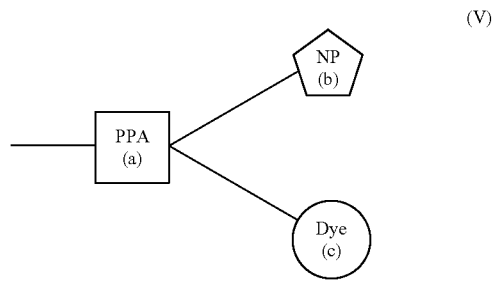

(V)

As will be appreciated, the dye, NP and PPA can be in any of the positions (a), (b), or (c) in the exemplary embodiment pictured in scheme (V).

Also encompassed by the invention are linear and branched molecules that comprise photoprotective agents which are incorporated into either the dye or the nucleoside polyphosphate moieties themselves. As will be appreciated, the description of the photoprotective agent as "incorporated" in the dye or the nucleoside polyphosphate moieties refers generally to the photoprotective agent as part of the structure of either moiety. Such incorporation can be accomplished using methods and techniques known in the art.

Forming the Conjugates

Conjugates of the invention can be formed using methods known in the art. In a preferred embodiment, linkers are derived from molecules which comprise a reactive functional group on each terminus, and these reactive functional groups can react with complementary reactive functional groups on the dye and/or the nucleotide.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds. ORGANIC FUNCTIONAL GROUP PREPARATIONS, Academic Press, San Diego, 1989).

In one embodiment, a first reaction partner includes a nucleophilic group (e.g., a thiol group, a thiophosphate group, an amino group and the like) and a second reaction partner includes an electrophilic group, such as an iodoacetamide group, an activated ester (e.g., NHS ester), an acid chloride, and the like. In one embodiment, thiol-iodoacetamide coupling chemistry is used to form conjugates of the invention. Coupling reactions between iodoacetamide derivatives and thiol derivatives are versatile due to the extreme nucleophilicity of the sulfhydryl group and the extreme electrophilicity of the iodoacetamide group. In one embodiment, the thiol-iodoacetamide coupling reaction is performed without the protection of other nucleophiles (e.g., amino groups) that are present in the reaction partners.

Figure 2:
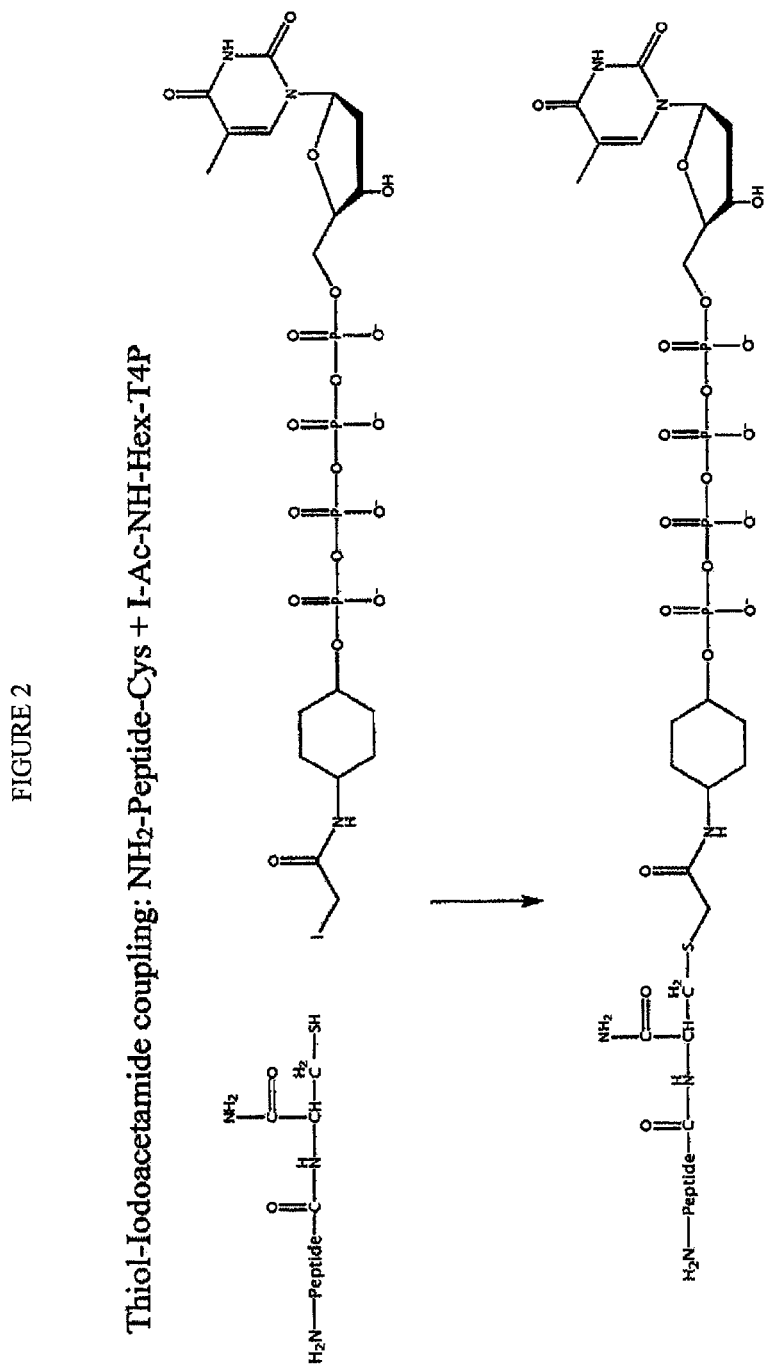
FIG. 2 is a scheme outlining an exemplary coupling reaction between a linking moiety and a peptide moiety of the invention.

In one example, a linker moiety, which is optionally bound to a nucleoside-phosphate analog, comprises an iodoacetamide moiety. The linker is reacted with a peptide moiety having a free thiol group to afford a nucleoside phosphate linked to a peptide moiety. An exemplary coupling reaction according to this embodiment is illustrated in FIG. 2. In FIG. 2, a peptide having a C-terminal cysteine residue is reacted with a linker moiety including an iodoacetamide group to afford a peptide moiety covalently linked to a phospho-nucleoside via a linker moiety, wherein the peptide moiety includes a nucleophilic group (e.g., a thiol group) and wherein the linking moiety includes an electrophilic group, such as an iodoacetamide group. In one exemplary embodiment, the linking moiety is optionally linked to a nucleoside polyphosphate moiety.

In another embodiment, a linker is covalently bound to a dye molecule through a peptide moiety. Linkage of the dye molecule, the linker moiety and the peptide moiety can occur in any order. In one embodiment, the linker moiety and the peptide moiety are covalently linked to each other first. The peptide moiety of the resulting peptide-linker molecule is than bound to a dye molecule. In another embodiment, the dye molecule comprises or is conjugated to the peptide moiety, and this compound is then covalently bound to the linker through the peptide moiety. The coupling between the components, e.g., between the peptide moiety and the linker moiety, can be accomplished using methods known in the art and described herein.

Figure 4:
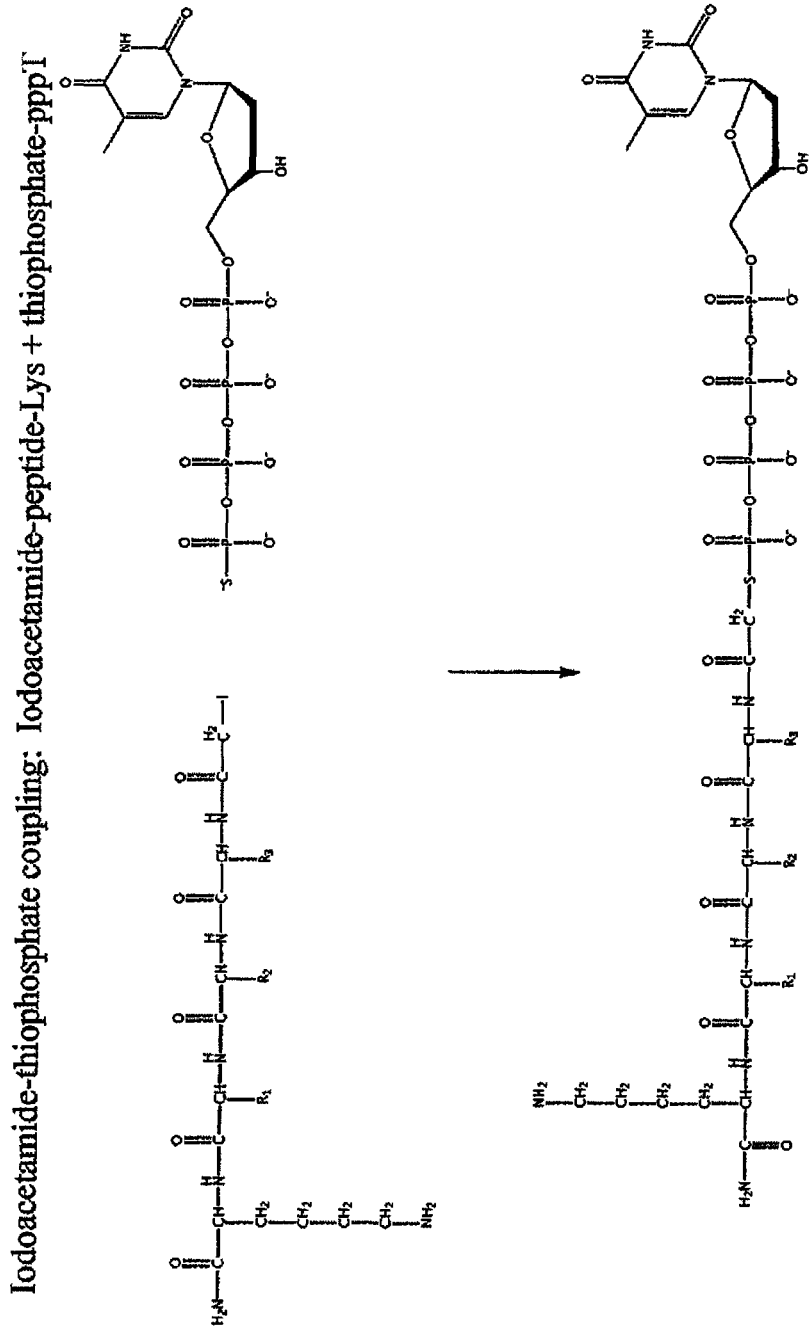
FIG. 4 is a scheme outlining an exemplary coupling reaction between a linking moiety or a peptide moiety and a nucleoside polyphosphate analog, wherein the nucleoside polyphosphate analog includes a nucleophilic group (e.g., a thiophosphate group) and wherein the linking moiety or the peptide moiety includes an electrophilic group, such as an iodo-acetamide group.

In another exemplary method, one of the reaction partners includes an iodoacetamide group, while another reaction partner includes a thio-phosphate group. For example, a peptide moiety including an iodoacetamide group is reacted with a nucleoside phosphate, in which a terminal phosphate residue is a thio-phosphate. An exemplary method according to this embodiment is illustrated in FIG. 4. In FIG. 4, a peptide moiety with an N-terminal iodoacetamide group is contacted with a nucleoside tetraphosphate in which the terminal phosphate unit is a thiophosphate group (e.g., thiophosphate-PPP-thymidine). The product from such a reaction can then be further modified to incorporate photoprotective agents. In one example, at least one of $R_1$, $R_2$ and $R_3$ in FIG. 4 includes a photoprotective agent. In another example, a photoprotective agent is covalently linked to the C-terminal lysine residue of the peptide moiety, e.g., via the amino group of the lysine side chain.

Figure 3:
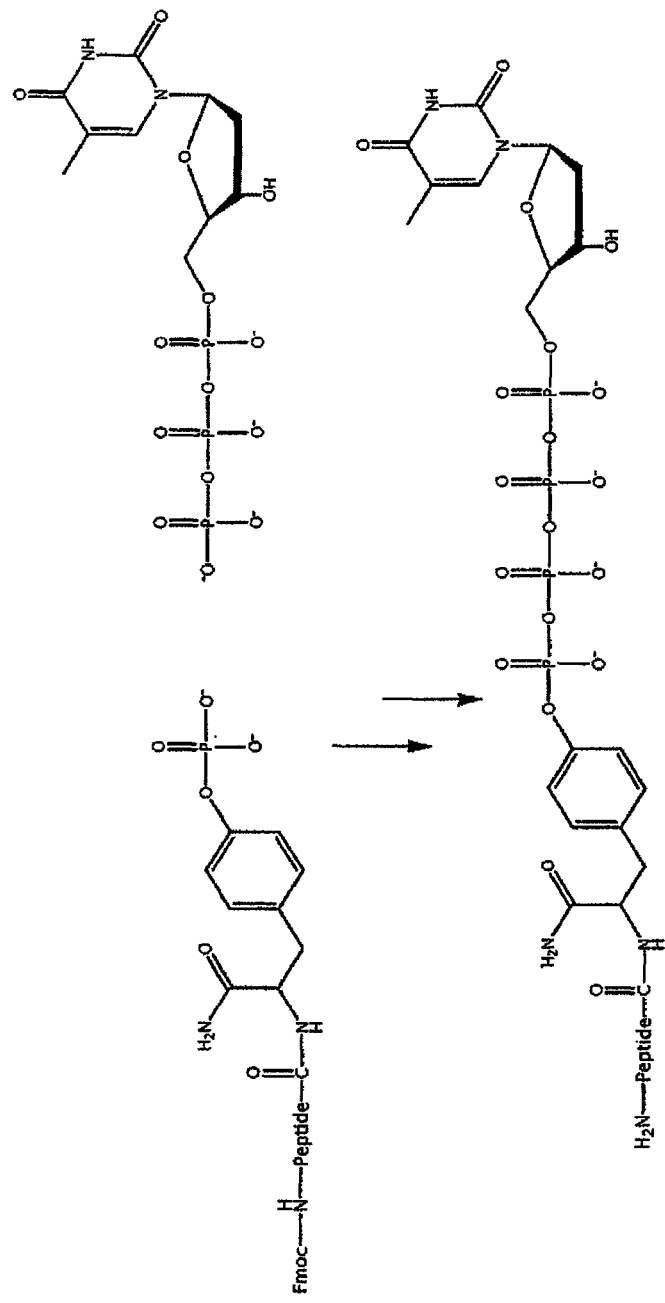
FIG. 3 is a scheme outlining an exemplary coupling reaction between a nucleoside polyphosphate and a linking moiety of the invention.

In yet another exemplary method, conjugation is accomplished through coupling of two terminal phosphate groups. For example, a nucleoside polyphosphate, such as a nucleoside triphosphate (e.g., thymidine tri-phosphate, TTP) is reacted with a peptide moiety having an amino acid residue with a hydroxyl group that is modified to include a phosphate group. Exemplary peptide moieties useful in this embodiment include a Ser-O-phosphate, a Thr-O-phosphate, a Tyr-O-phosphate or a hydroxyproline-O-phosphate moiety. An exemplary coupling reaction according to this embodiment is illustrated in FIG. 3. In FIG. 3, an Fmoc-protected peptide moiety that contains a phospho-tyrosine residue is reacted with a nucleoside triphosphate to form a nucleoside tetraphosphate linked to a peptide moiety via a tyrosine linker.

Figure 5:
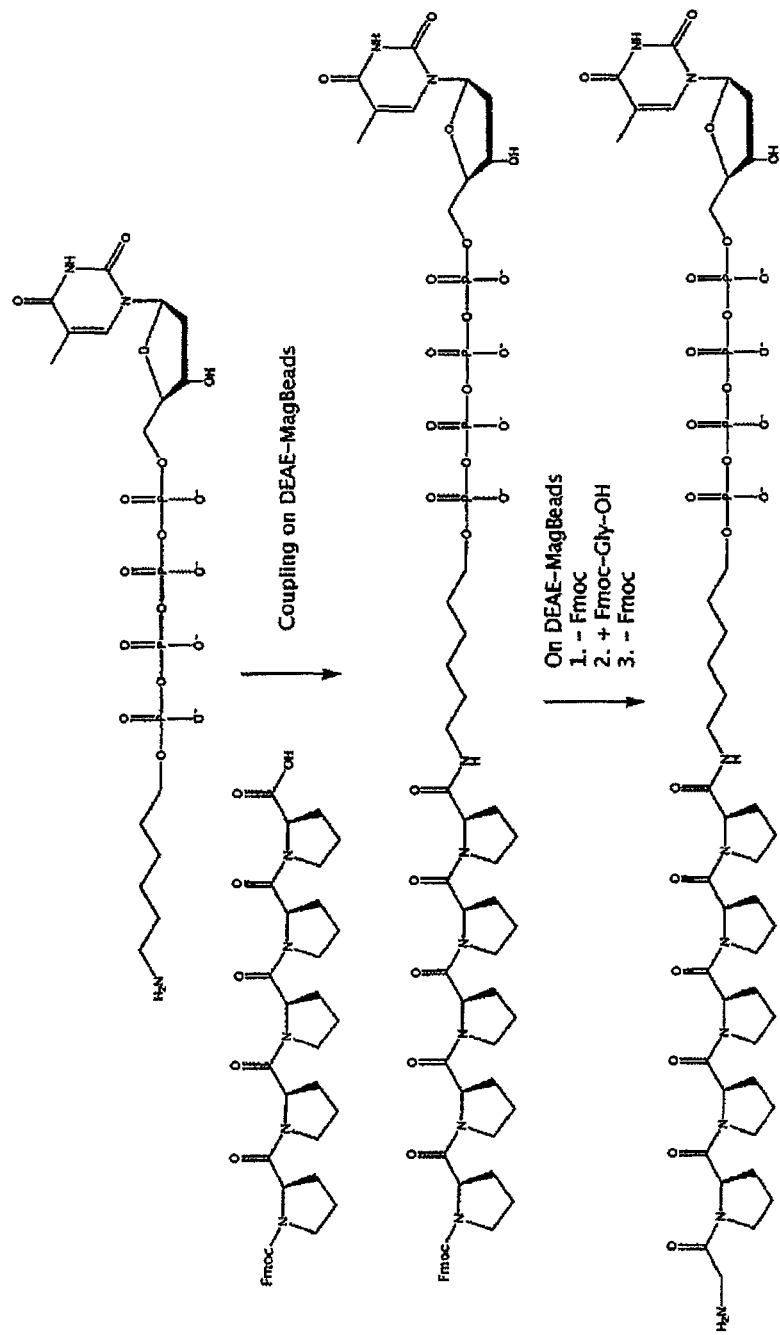
FIG. 5 is a scheme outlining an exemplary peptide coupling reaction between a nucleoside polyphosphate analog and a N-terminally protected poly(amino acid), such as polyproline (e.g., Fmoc-Pro$_5$-OH).

In still another exemplary embodiment, the reactants are covalently linked through the formation of an amide bond. Peptide coupling reactions are well known in the art and are typically performed in the presence of a peptide coupling reagent, such as EDC, HATU, HBTU, PyBOP and HOBt. In one example, an N-terminally protected peptide moiety is contacted with a nucleoside phosphate analog that includes a free amino group in the presence of a peptide coupling reagent. An exemplary method according to this embodiment is illustrated in FIG. 5. In FIG. 5, coupling is carried out between a nucleoside polyphosphate analog and a N-terminally protected poly(amino acid), such as poly-proline (e.g., Fmoc-Pro$_5$-OH), wherein the nucleoside polyphosphate analog includes an amino group. The amino group may be introduced by pre-coupling of a nucleoside polyphosphate to an alkyl amine analog. In one embodiment, coupling is facilitated through the presence of an anion exchange resin (e.g., DEAE-MagBeads). Additional amino acid residues are optionally coupled to the N-terminus of the peptide moiety (e.g., poly(amino acid) moiety), for example, by first removing the protecting group (e.g., Fmoc group) and contacting the de-protected peptide with an Fmoc-amino acid (e.g., Fmoc-Gly-OH) in the presence of a coupling reagent. Alternatively (or in addition), the Fmoc group is removed and the peptide moiety is linked to a fluorescent dye molecule.

Linkers

The term "linker" or "linker moiety" encompasses any moiety that is useful to connect a reporter molecule (e.g., a fluorescent dye molecule) to a nucleotide (e.g., a deoxynucleotide). In one embodiment, the linker is a member selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl. In one example, the linker moiety is selected from straight- and branched carbon-chains, optionally including at least one heteroatom (e.g., at least one functional group, such as ether, thioether, amide, sulfonamide, carbonate, carbamate, urea and thiourea), and optionally including at least one aromatic, heteroaromatic or non-aromatic ring structure (e.g., cycloalkyl, phenyl).

The linker as a whole may comprise a single covalent bond or a series of stable bonds. Thus, a reporter molecule (such as a fluorescent dye) may be directly attached to another reactant, such as a nucleoside polyphosphate, or the reporter molecule may be attached to a nucleoside polyphosphate through a series of stable bonds. A linker that is a series of stable covalent bonds can incorporate non-carbon atoms, such as nitrogen, oxygen, sulfur and phosphorous, as well as other atoms and combinations of atoms, as is known in the art.

If the linker is not directly attached to a reactant by a single covalent bond, the attachment may comprise a combination of stable chemical bonds, including for example, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In an exemplary embodiment, the dye is conjugated to the nucleoside triphosphate as an alkylated tetraphosphate analog. Exemplary linker moieties are shown in FIG. 1. The structures in FIG. 1 are exemplary and are not meant to be limiting as to the linking moieties that can be used in accordance with the invention. In FIG. 1, X in exemplary structures (i)-(iv) represents without limitation a halogen, a tosylate, a mesylate, or any other leaving group known in the art. In exemplary structure (ii) in FIG. 1, $(P)_n$ represent phosphate groups and n is an integer from 1 to 50.

In one embodiment, the linker incorporates a photoprotective agent (e.g., a triplet quencher). In one example, the linker moiety is substituted with a moiety that includes a photoprotective agent. Photoprotective agents can be incorporated into the linker using methods known in the art and as described herein.

Length and Configuration of Linkers

The length of a linker can affect the ability of the dye and the nucleotide to perform their designated functions in a reaction. For example, a dye molecule linked to a nucleoside polyphosphate must be at a proper distance and in the correct configuration to provide a detectable signal when that nucleoside polyphosphate has been added to a nucleic acid strand. In addition, any photoprotective agents incorporated into the linker must also be at the proper distance and configuration (i.e., at a "close spatial proximity") to be able to prevent damage to the reactants resulting from illumination.

The present invention provides methods and compositions for determining the optimal linker length for use in illuminated reactions, such as sequencing reactions. In one embodiment, poly-L-proline oligomers are used as "molecular rulers". A stretch of proline residues forms a stable helical structure, the polyproline II helix. Addition of each proline residue increases the length of this helix in a predictable manner—approximately 3 angstroms per proline residue. (see Arora et al., *J. Am. Chem. Soc.* (2002) 124:13067-13071). Thus, a linker comprising a series of prolines can be used to provide a known distance between a dye molecule and a nucleoside polyphosphate. In addition, poly-proline oligomers inserted between residues of interest can provide predictable positioning of the side groups of the intervening amino acids. Such peptides can be synthesized using methods known in the art. (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference).

Other moieties can be used in a similar manner to provide a known distance between a dye and a nucleoside polyphosphate. For example, the linking moieties listed in FIG. 1 represent commercially available reagents that can be used to provide a known length between the dye and the nucleoside polyphosphate. In other embodiments, the linker comprises different units of moieties, i.e., a "chain" of moieties, wherein each unit is a link in that chain. In one embodiment, a photoprotective agent is integrated into the chain of a linker as one of the component links. The "units" of the links of the chain may comprise one or more moieties repeated over the length of the chain, or each unit link may be a different moiety.

In order to determine the optimal distance between the dye molecule and a mitigating agent, such as a triplet state quencher, the dye molecule can be coupled to the quencher using various linker moieties. Exemplary molecules according to this embodiment and methods for their synthesis are shown in FIG. 6 and FIG. 9, which are discussed below.

Figure 6:
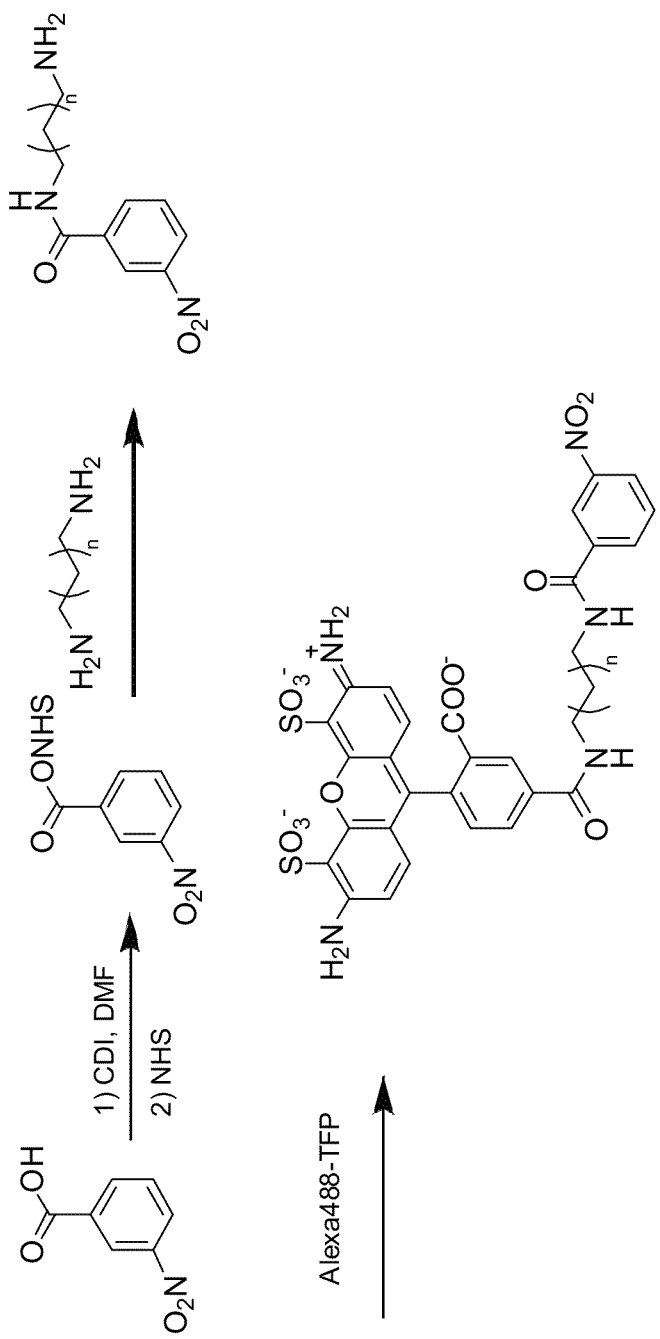
FIG. 6 is a scheme outlining an exemplary route for the synthesis of a compound of the invention. The product is an exemplary fluorescent dye molecule covalently linked to a triplet quencher moiety.

In FIG. 6, 3-nitrobenzoic acid (NBA) is converted to an NHS ester, which is subsequently reacted with a diamine, such as a diamino alkane (e.g., ethane-1,2-diamine, propane-1,3-diamine, butane-1,4-diamine, pentane-1,5-diamine, hexane-1,6-diamine, heptane-1,7-diamine and the like) to afford an intermediate amine. The free amino group of the intermediate is used for coupling to a dye molecule, optionally via an additional linker. In the embodiment pictured in FIG. 6, the linker may have a variable length of "n". As will be appreciated, "n" is chosen to provide an optimal distance between the dye and the mitigating agent. In one embodiment, n has a value from about 1 to about 50, from about 2 to about 45, from about 3 to about 40, from about 4 to about 35, from about 5 to about 30, from about 10 to about 25, and from about 15 to about 20. In a further embodiment, n has a value from about 1 to about 20, from about 2 to about 15, from about 3 to about 10, and from about 4 to about 8.

Figure 9:
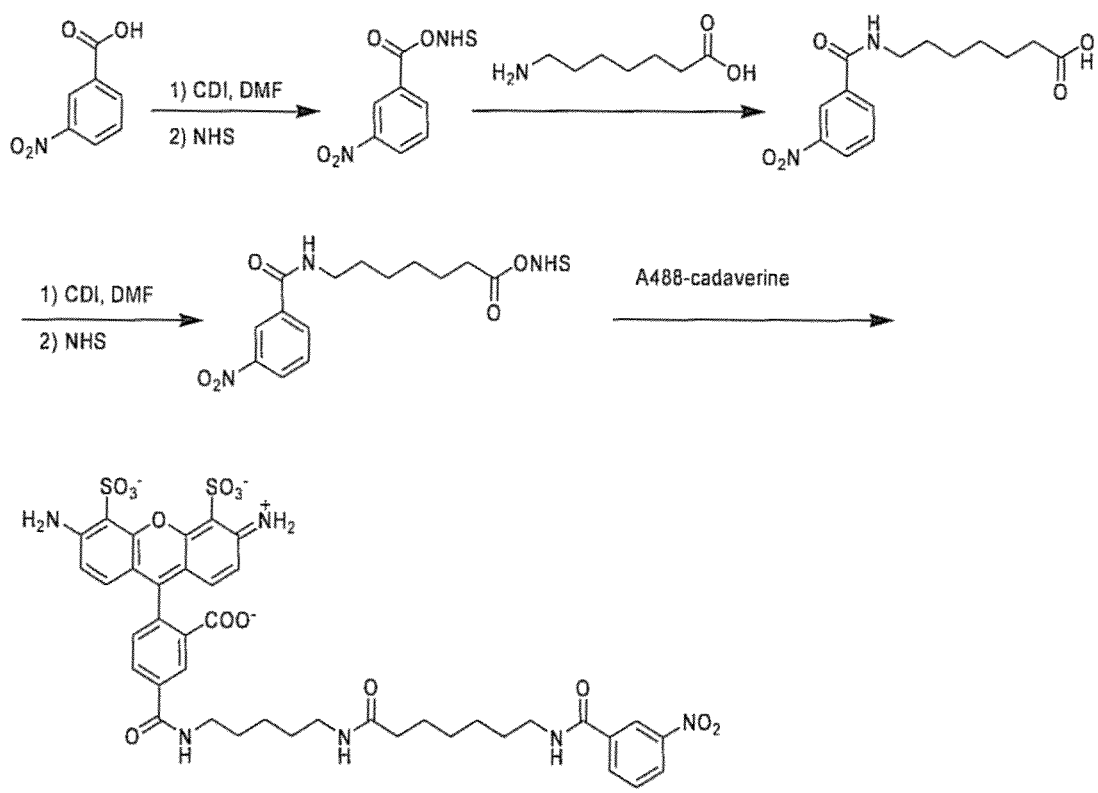
FIG. 9 is a scheme outlining an exemplary route for the synthesis of a compound of the invention. The product is an exemplary fluorescent dye molecule covalently linked to a triplet quencher moiety.

In FIG. 9, 3-nitrobenzoic acid NHS ester is reacted with a linker molecule, such as an amino alkanoic acid (e.g., 3-aminopropanoic acid, 4-aminobutanoic acid, 5-amino-pentanoic acid, 6-aminohexanoic acid or 7-aminoheptanoic acid and the like) to afford an intermediate carboxylic acid. The intermediate is activated, e.g., through conversion to an activated ester (e.g., NHS-ester) and is subsequently reacted with a dye molecule that includes an amino group. For example, the dye molecule is derivatized with an alkyl amine. An exemplary modified dye molecule is Alexa 488 that is linked to an alkyl chain with a terminal amino group (e.g., Alexa 488 linked to cadaverin). One such molecule is the end result of the scheme pictured in FIG. 9, which is also referred to herein as "Alexa 488-HD-NBA. Such model compounds can be used to identify optimal linker lengths for particular dye molecules and particular dye molecule and nucleoside polyphosphate combinations.

In another embodiment, the optimal length is provided by varying the number of phosphate groups between the nucleoside and the linker, dye, or photoprotective agent. In an exemplary embodiment illustrated in FIG. 7, the number of phosphate groups "x" can be any range of values that provides the optimal length between, in this example, between the nucleoside and the linker. In other embodiments, the phosphate groups may be between the nucleoside and the dye, or between the nucleoside and a photoprotective agent. In one example, about 1 to about 20 phosphate groups are used to separate the nucleoside and the linker, dye or photoprotective agent. In another example, about 3 to about 20, about 4 to about 15, and about 5 to about 10 phosphate units are used to separate the nucleoside and the linker, dye or photoprotective agent. In another exemplary embodiment, 3 to 10 phosphate units are used. In a particularly preferred embodiment, 3 to 5 phosphates are used.

Dye molecules, such as fluorescent dyes, as well as their activated analogs and derivatives, are known in the art (see e.g., Invitrogen, *The Handbook—A Guide to Fluorescent Probe and Labeling Technologies*). Exemplary dyes are described herein, below. In one example, the fluorescent dye is Alexa 488. A person of skill in the art will appreciate that NBA, which is used as an exemplary quencher in FIG. 6 and FIG. 9 discussed above, can be replaced with another quencher, such as those disclosed herein. A skilled person will also be able to replace the amino alkanoic acid linker (FIG. 9) and the alkane-diamine linker (FIG. 6) with another linker. Exemplary alternative linkers include alkenes, substituted cycloalkyl groups (e.g., substituted cyclohexyl), substituted heterocycloalkyl (e.g., piperidinyl, morpholinyl or piperazinyl) substituted aryl groups (e.g., phenyl) and substituted heteroaryl groups.

Incorporating Photoprotective Agents into Linkers and Binding Linkers to Dyes and/or Nucleotides Incorporation of photoprotective agents into the linker moiety can be accomplished using methods known in the art and those described herein.

In one example, the linker is substituted with a moiety that includes a triplet quencher, such as those described herein. In one exemplary embodiment, the triplet quencher includes a nitrobenzoic acid (NBA) moiety.

Figure 7:
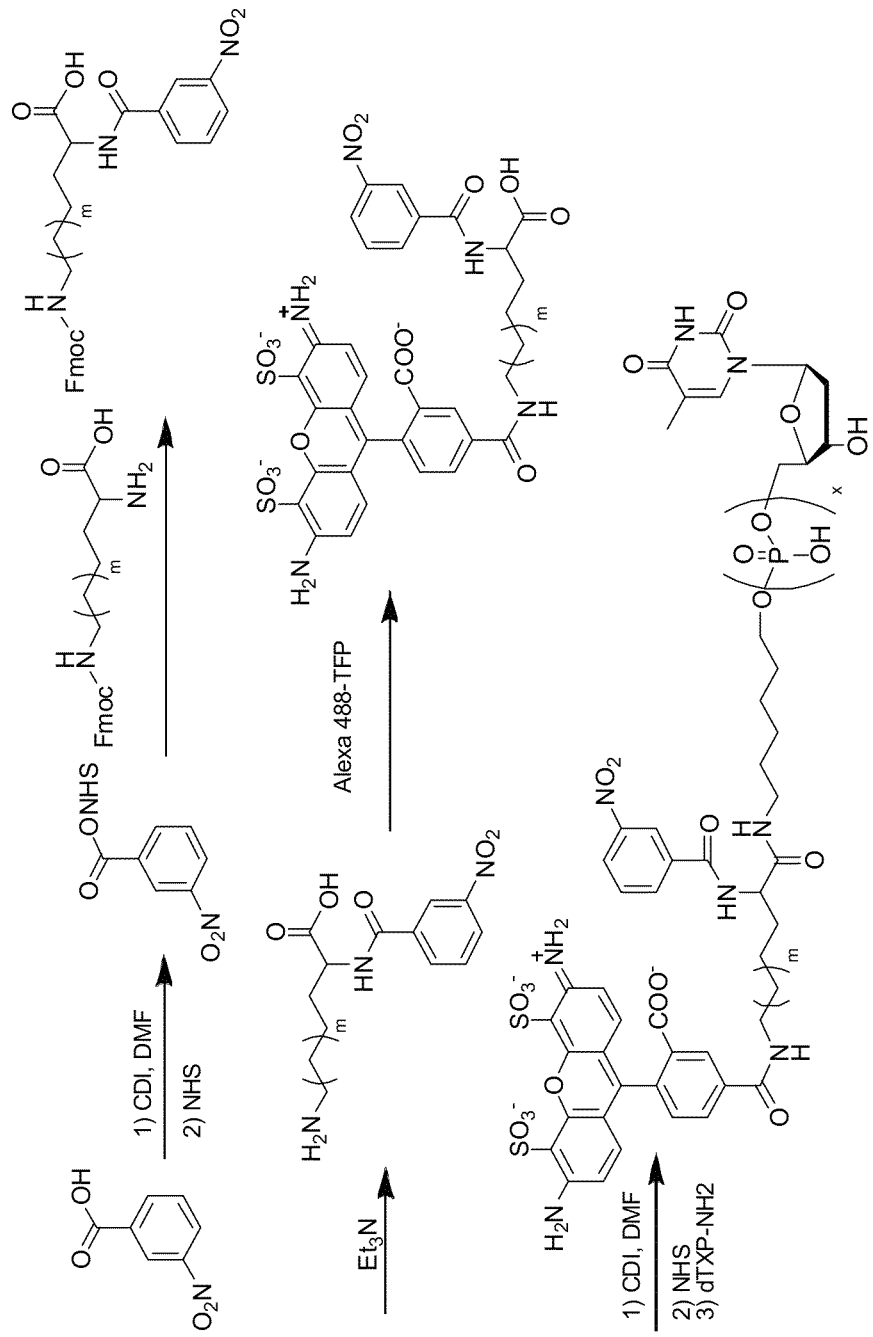
FIGS. 7 and 8 provide schemes outlining exemplary routes for the synthesis of compounds of the invention.
Figure 8:
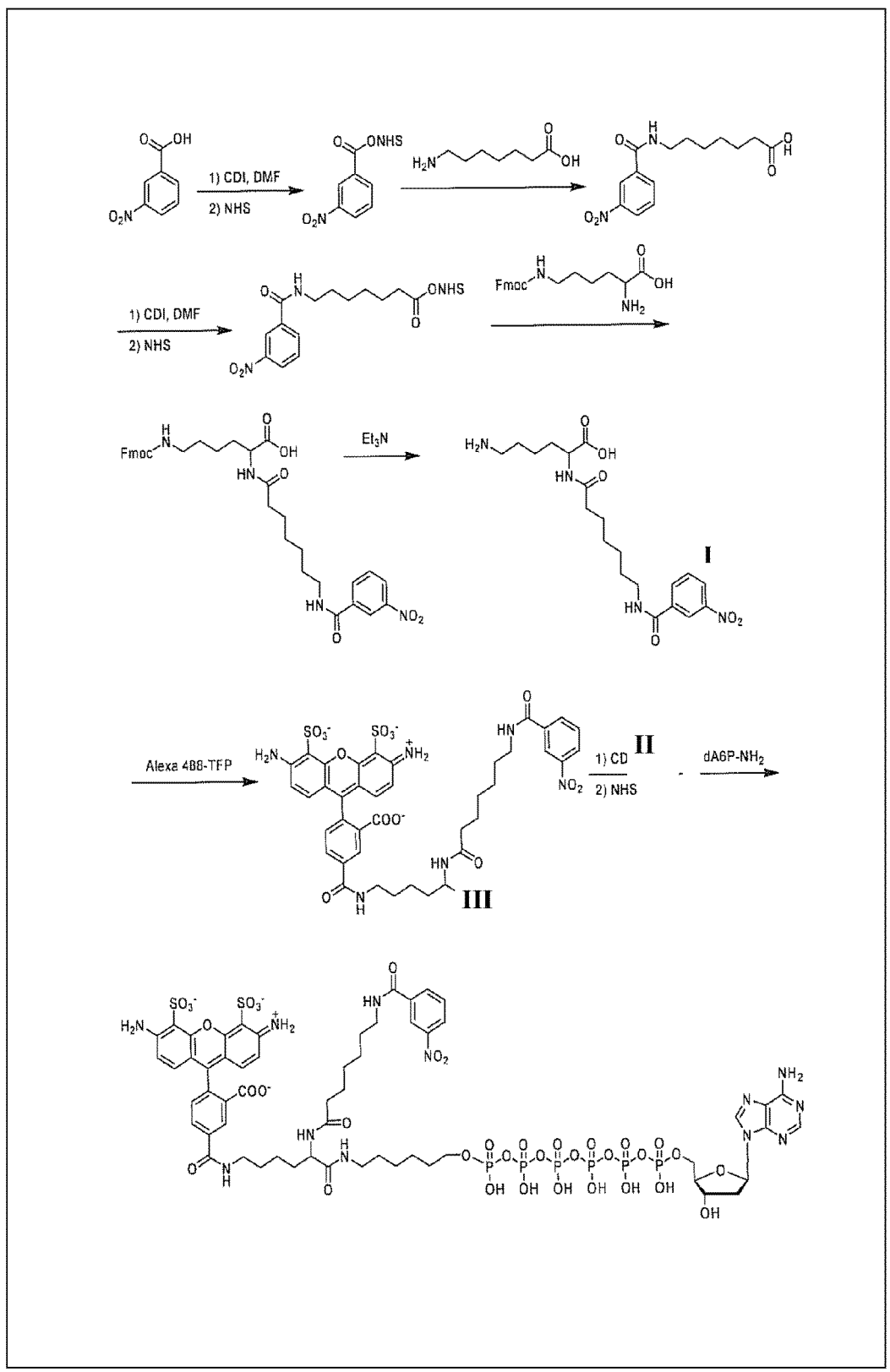

Exemplary methods for the synthesis of a dye-labeled nucleoside polyphosphate including a linker moiety substituted with a triplet quencher are illustrated in FIGS. 7 and 8. In FIG. 7, 3-nitrobenzoic acid (NBA) is converted to the respective NHS ester, which is subsequently reacted with an amino alkanoic acid of varying lengths, (e.g., 3-aminopropanoic acid, 4-aminobutanoic acid, 5-amino-pentanoic acid, 6-aminohexanoic acid or 7-aminoheptanoic acid and the like) to produce the compound in which the quencher is attached to the linker (the amino alkanoic acid). The "m" in FIG. 7 can be chosen to provide the optimal linker length. In one embodiment, m has a value from about 0 to about 50, from about 1 to about 45, from about 2 to about 40, from about 3 to about 35, from about 4 to about 30, from about 5 to about 25, and from about 10 to about 20. In a further embodiment, m has a value from about 1 to about 20, from about 2 to about 15, from about 3 to about 10, and from about 4 to about 8. In one embodiment, m has a value of about 1.

A person of skill in the art will appreciate that NBA as the quencher is exemplary and can be replaced with other quenchers disclosed herein. A skilled person will also be able to replace the amino alkanoic acid with another linker that includes an amino group as well as a carboxylic acid functionality. Exemplary alternative linkers include alkenes, substituted cycloalkyl groups (e.g., substituted cyclohexyl), substituted heterocycloalkyl (e.g., piperidinyl, morpholinyl or piperazinyl) substituted aryl groups (e.g., phenyl) and substituted heteroaryl groups.

FIG. 8 provides another exemplary embodiment for the synthesis of a dye-labeled deoxynucleotide. In FIG. 8, the carboxylic acid group of compound I is activated, e.g., through conversion to an activated ester (e.g., NHS-ester) and is subsequently reacted with a molecule that provides a "branching point", such as a protected lysine residue, to afford compound II. The protecting group (e.g., Fmoc group) of compound II is removed and the deprotected amino group is used to couple the molecule to an activated (e.g., tetrafluorophenyl ester (TFP)-activated) dye molecule to afford compound III. Dye molecules, such as fluorescent dyes, as well as their activated analogs, are known in the art (see e.g., Invitrogen, *The Handbook—A Guide to Fluorescent Probes and Labeling Technologies*). Exemplary dyes are described herein. In one exemplary embodiment, the fluorescent dye is Alexa 488.

In FIG. 8, the carboxylic acid group of compound III is activated through conversion to an activated ester (e.g., NHS ester) and coupled to a deoxy-nucleotide that is functionalized with an amine. As will be appreciated, a nucleoside polyphosphate used in accordance with the invention may be a modified nucleotide that includes multiple phosphate groups, as illustrated in FIG. 7 as "x". As discussed above, in FIG. 7, "x" may be a range of values from about 1 to about 20. In a particular embodiment, the nucleotide is selected from a nucleoside triphosphate, a nucleoside tetraphosphate, a nucleoside pentaphosphate, a nucleoside-hexaphosphate, a nucleoside heptaphosphate and a nucleoside octaphosphate. An exemplary product is represented by compound IV in FIG. 8. One of skill in the art will appreciate that the nucleoside polyphosphate base can be of any naturally occurring or non-naturally occurring analog of a nucleotide.

Figure 10:
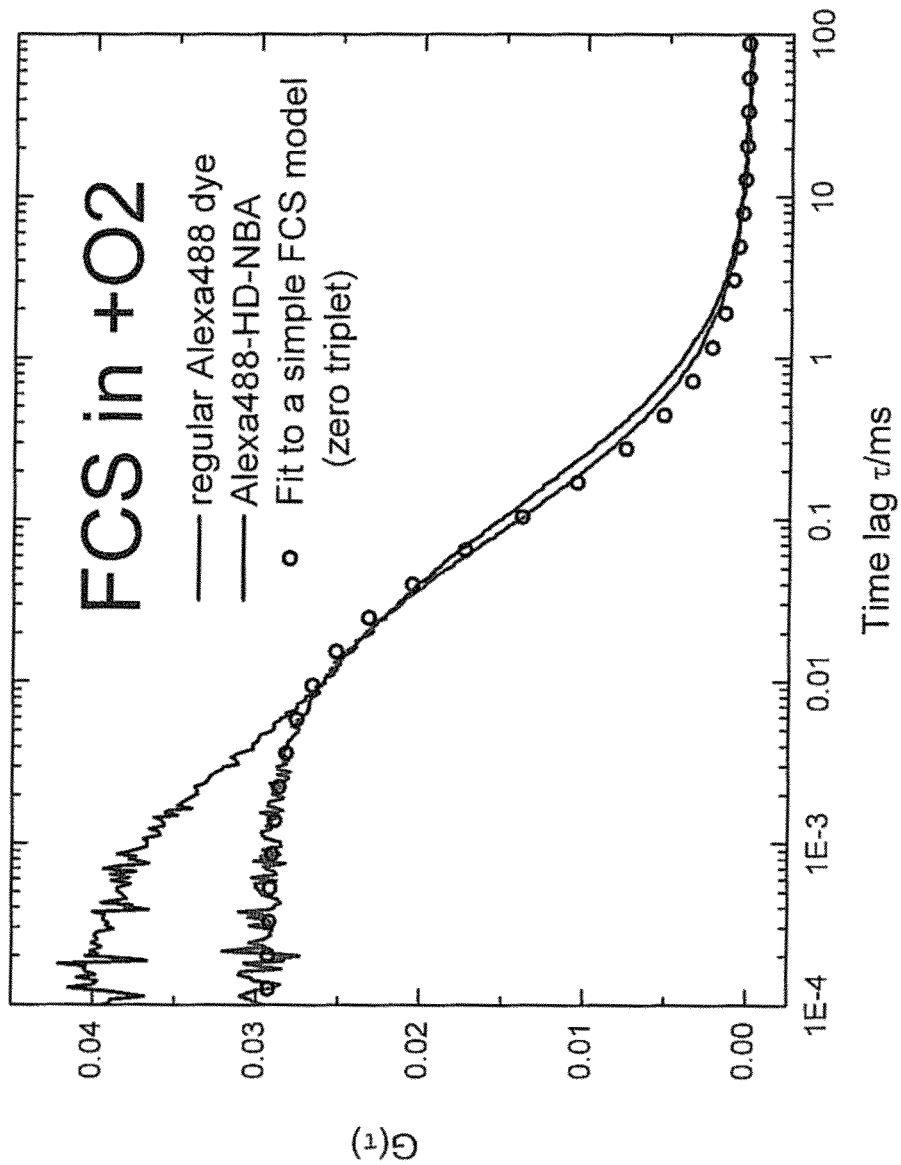
FIG. 10 is a diagram obtained by fluorescence-correlation spectroscopy and comparing the fluorescent properties of a control dye ("regular Alexa488 dye") and a molecule of the invention (Alexa488-HD-NBA).
Figure 11:
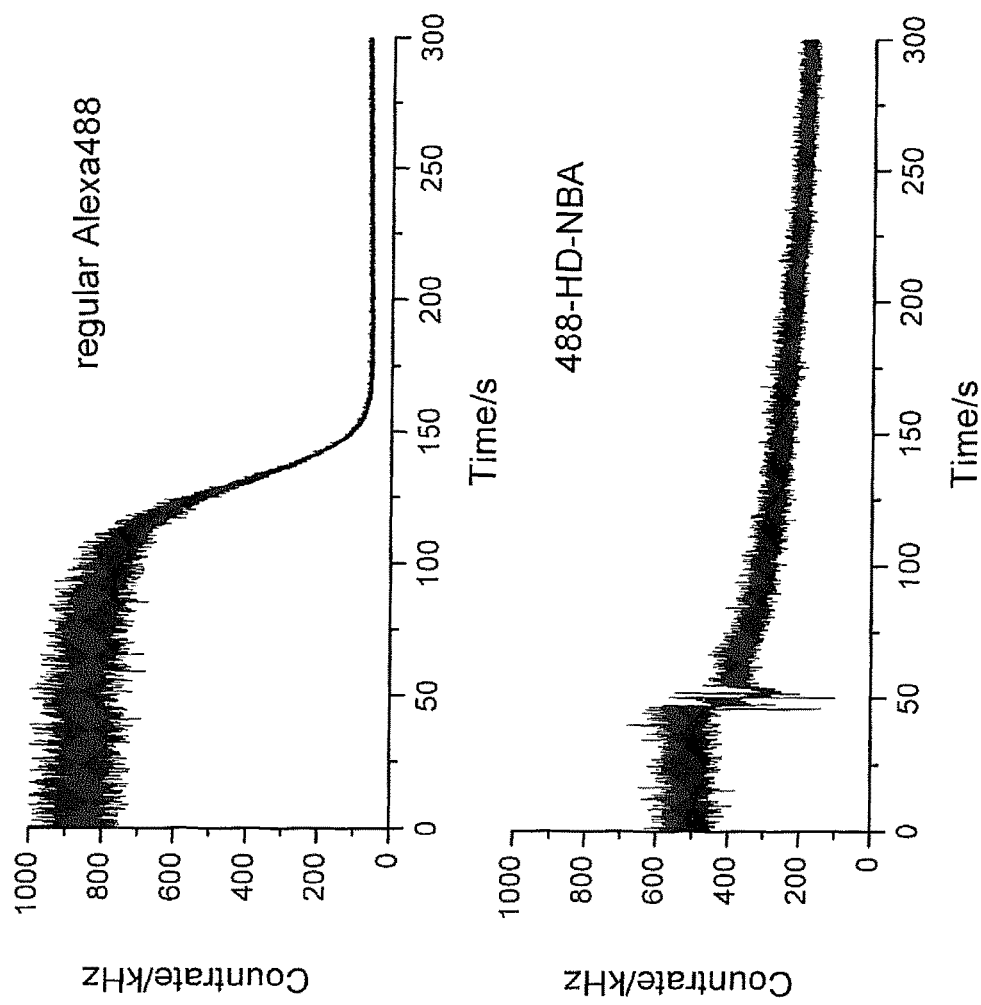
FIG. 11 shows fluorescent time traces of a control dye ("regular Alexa 488") and a molecule of the invention ("488-HD-NBA").
Figure 12:
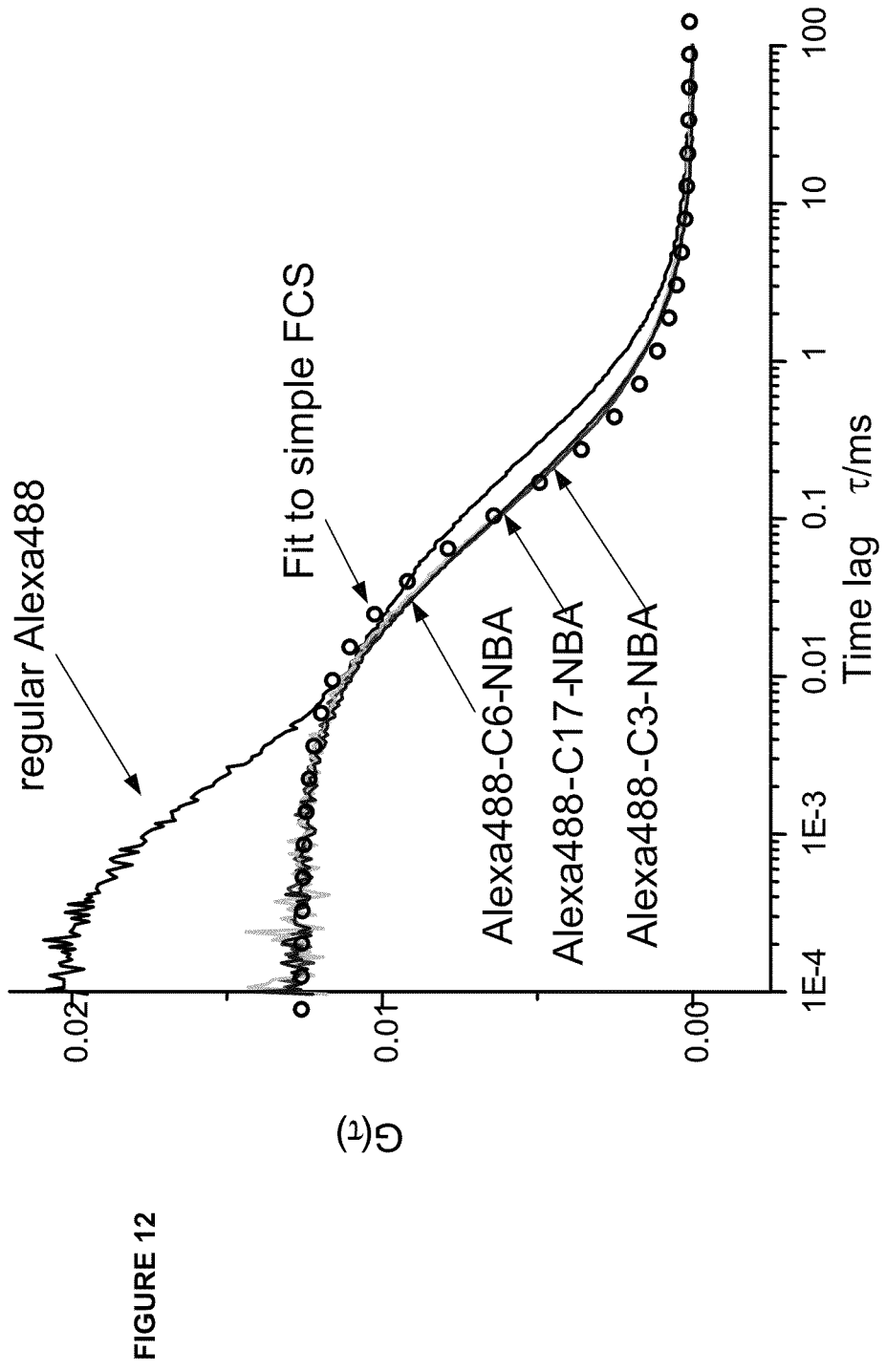
FIG. 12 shows fluorescence correlations spectroscopy curves from different compounds of the invention.

An exemplary method for determining whether a linker is of optimal length and/or configuration is through use of fluorescence correlation spectroscopy. FIGS. 10-12 provide such measurements for compounds of the invention. Molecular brightness data are provided for different conjugates of the invention in Table I. As is shown in FIGS. 10-12 and Table I, the "Alexa-HD-NBA" conjugate, which is the conjugate pictured in FIG. 9, is more effective at mitigating photodamage and allowing the dye to stay brighter longer than the other conjugates represented in the figures.

TABLE I

|  | Regular Alexa488 | Alexa488-HD-NBA | Alexa488-C3-NBA | Alexa488-C17-NBA |
|---|---|---|---|---|
| OD 2.0 | 14.2 kHz | 15.5 kHz | 10.7 kHz | 6.58 kHz |
| OD 1.4 | 23.4 kHz | 41.6 kHz | 29.2 kHz | 20.9 kHz |

Dye Molecules

As used herein and unless otherwise indicated, the term "dye" or "dye molecule" refers to a detectable molecule. Such dyes are part of conjugates made according to the invention as described herein.

Exemplary molecules that are dyes in accordance with the present invention include but are not limited to fluorescent molecules (e.g. fluorescein), luminescent moieties (e.g., transition-metal complexes), chemiluminescent molecules, molecules used in colorimetric applications, histochemical staining reagents, photoaffinity labels, and radioactive labels.

In addition to a detectable molecule, the term dye can also refer to a molecule that modulates detection of another detectable molecule, (e.g., a quencher). As used herein, the term "detectable label" is intended to include not only a molecule or label which is "directly" detected (e.g., a chromogen or a fluorophore) but also a moiety (e.g., biotin) which is "indirectly" detected by its binding to a second, third, or greater binding partner (e.g., avidin or streptavidin), one of which carries a "direct" label.

In a preferred embodiment, the dye is a fluorescent dye, and in a particularly preferred embodiment the fluorescent dye comprises a fluorescent labeling group. Fluorescent dyes are molecules, which, when exposed to light of the proper wavelength, becomes detectable due to fluorescence and is detected and/or measured by microscopy or fluorometry. Commonly used fluorescent dyes and/or fluorescent labeling groups include fluorescein isothiocyanate, rhodamine, phycoerythrin, phycocyanin, allophycocyanin, .gamma.-phthalaldehyde and fluorescamine. The dye can be a fluorescence-emitting metal such as $^{152}$Eu, or others of the lanthanide series which can be attached to another molecule using metal chelating groups, such as diethylenetriaminepentaacetic acid or ethylenediaminetetraacetic acid. In one embodiment, a dye of the "Alexa" family of dyes is used, including without limitation Alexa 350, Alexa 430, Alexa 488, Alexa 532, Alexa 546, Alexa 568, and Alexa 594 dyes. In a particularly preferred embodiment, an Alexa dye is used in combination with NBA as the photoprotective agent in conjugates of the invention.

The term dye can also refer to a chemiluminescent compound, the presence of which is detected by measuring luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound can be used to label a molecule and is detected by measuring luminescence. In this case, a catalytic protein increases the efficiency of the chemiluminescence reaction. Examples of useful bioluminescent labeling compounds include luciferin, luciferase and aequorin.

Nucleoside Polyphosphates

As described herein, one component of conjugates of the invention is a nucleoside polyphosphate. In an exemplary embodiment, the conjugates comprise a nucleoside triphosphate. The term "nucleoside triphosphate" as used herein refers to the so-called "building blocks" of DNA and RNA. "Nucleoside triphosphate" is used interchangeably with the terms "nucleotide" and "nucleic acid" as used herein. Nucleotides that contain a ribose sugar are the monomers of RNA and those that contain a deoxyribose sugar compose DNA. Although the following exemplary embodiments refer to nucleoside triphosphates, it will be appreciated that any of the embodiments described herein may also refer to other nucleoside polyphosphates, including nucleoside tetraphosphates, nucleoside pentaphosphates, nucleoside hexaphosphates and longer nucleoside phosphates (i.e., nucleoside polyphosphates with seven or more phosphates in the phosphate chain).

Nucleotides included in conjugates of the invention as described herein can be DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications can also include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole; such nucleic acids may also be referred to as bases of non-naturally occurring nucleotide mono- and higher-phosphates. Modifications can also include 3' and 5' modifications such as capping with a quencher, a fluorophore or another moiety.

The present invention also encompasses conjugates that include nucleotide derivatives and products thereof. Exemplary nucleotide derivates are nucleotides which form hydrogen bonds with a complementary nucleotide on a template nucleic acid, but comprise a modification that prevents the formation of a phosphodiester bond with the 3' hydroxyl group of the primer. Preferred nucleotide derivatives will be recognized by the catalytic domain of the polymerase and brought in close proximity with its complementary nucleotide where hydrogen bonding can occur. Accordingly, nucleotide derivatives which are particularly useful for synthesis of nucleic acids, nucleic acid fragments, and oligomers, most closely resemble naturally-occurring substrates for polymerases in both chemical formula and structure.

In an exemplary embodiment, a nucleotide derivative comprises a modification of the oxygen bridging the α-phosphate and the β-phosphate in a standard nucleotide triphosphate. For example, preferred modifications include the substitution of the oxygen molecule bridging the α- and β-phosphate groups with a carbon, nitrogen or sulfur molecule or a methylene group. Other nucleotide derivatives useful in the invention comprise a modification of the α-, β- or γ-phosphate group, such as, for example, the substitution of a bridging or non-bridging oxygen molecule with a thiol, alkyl, carbonyl, amine, alcohol, aryl or an amino acid group; or a bulky group that physically interferes with polymerase function. In the case of polyphosphates with more than three phosphate groups in the chain, it will be appreciated modifications on any of the phosphates beyond the α-, β- or γ-phosphate groups are also encompassed by the present invention. Custom modified nucleotides are commercially available from, for example, TriLink BioTechnologies, Inc., San Diego, Calif., Alexis Biochemicals, Inc., Carlsbad, Calif. and BIOLOG Life Science Institute, Germany.

Exemplary Applications

As noted above, the methods and compositions of the invention are useful in a broad range of illuminated analytical reactions, particularly those using photoluminescent or fluorescent reactants. One exemplary application of the methods and compositions described herein is in single molecule analytical reactions, where the reaction of a single, (or a limited number of) molecules are observed in the analysis—for example, the observation of the action of a single enzyme molecule. In particular, when an analysis relies upon a small population of reagent molecules, damage to any significant fraction of that population will have a substantial impact on the analysis being performed. The linkers of the present invention can prevent or mitigate that impact by providing photoprotective agents in the reaction mixture.

One example of a single molecule analysis includes sequencing of nucleic acids by observing incorporation of nucleotides into a nascent nucleic acid sequence during template directed polymerase based synthesis. Such methods, generally referred to as "sequencing by incorporation," involve observing the addition of nucleotides or nucleotide analogs in a template dependent fashion in order to determine the sequence of the template strand. Processes for performing this detection include the use of fluorescently labeled nucleotide analogs within a confined observation region, e.g., within a nanoscale well or tethered, either directly or indirectly to a surface. By using excitation illumination (i.e., illumination of an appropriate wavelength to excite the fluorescent label and induce a detectable signal), the fluorescently labeled bases can be detected as they are incorporated into the nascent strand, thus identifying the nature of the incorporated base, and as a result, the complementary base in the template strand.

In one embodiment, the sequencing by incorporation reactions that use conjugates and methods of the invention take place within an optical confinement, such as a zero mode waveguide. In such reactions, one is observing an extremely small reaction volume in which one or only a few polymerase enzymes and their fluorescent substrates may be present. Zero mode waveguides, and their use in sequencing applications are generally described in U.S. Pat. No. 6,917,726, and preferred methods of sequencing by incorporation are generally described in Published U.S. Patent Application No. 2003-0044781, the full disclosures of which are incorporated herein by reference in their entirety for all purposes, and in particular for their teachings regarding such sequencing applications and methods.

In general, conjugates of the invention as described herein are particularly suited to mitigating photodamage to reactants in small volume concentrations. Such limited quantity reagents or reactants may be present in solution, but at very limited concentrations, e.g., less than 200 nM, in some cases less than 10 nM and in still other cases, less than 10 pM. In preferred aspects, however, such limited quantity reagents or reactants refer to reactants that are immobilized, or otherwise confined within a given area, so as to provide limited quantity of reagents in that given area, and in certain cases, provide small numbers of molecules of such reagents within that given area, e.g., from 1 to 1000 individual molecules, preferably between 1 and 10 molecules. As will be appreciated, photodamage of immobilized reactants in a given area will have a substantial impact on the reactivity of that area, as other, non-damaged reactants are not free to diffuse into, and mask the damage effects.

As will be appreciated, the photodamage of illuminated reactions sought to be prevented by the methods and compositions of the invention is not merely photodamage to fluorescent reagents, e.g., photobleaching, but also includes the prevention or reduction of the downstream effects of photoactivation. In small volumes, reagents with a limited presence are greatly impacted by even slight losses due to photodamage, particularly reactive proteins or enzymes. This damage, without being bound to a theory of operation, may include damage to the enzymes or reactive proteins or irreversible interactions between such enzymes or proteins and the photodamaged reagents. Typically, such damage directly impacts either the reactant of interest, e.g., direct photodamage, or impacts a reactant within one, two or three reactive steps of such reactant of interest.

By way of example of the application of the invention to methods of performing sequencing reactions, U.S. Pat. No. 7,033,764 (which is incorporated herein by reference in its entirety for all purposes) describes single molecule DNA sequencing processes and systems that would benefit from the methods and devices described herein. Briefly, arrays of zero mode waveguides ("ZMWs"), configured in accordance with the present invention may be employed as optical confinements for single molecule DNA sequence determination. In particular, as noted above, these ZMWs provide extremely small observation volumes at or near the transparent substrate surface, also termed the "base" of the ZMW. A nucleic acid synthesis complex, e.g., template sequence, polymerase, and primer, which is immobilized at the base of the ZMW, may then be specifically observed during synthesis to monitor incorporation of nucleotides in a template dependent fashion, and thus provide the identity and sequences of nucleotides in the template strand. This identification is typically accomplished by providing detectable label groups, such as fluorescent labeling molecules, on the nucleotides. In some instances, the labeled nucleotides terminate primer extension, allowing a "one base at a time" interrogation of the complex. If, upon exposure to a given labeled base, a base is incorporated, its representative fluorescent signal may be detected at the base of the ZMW. If no signal is detected, then the base was not incorporated and the complex is interrogated with each of the other bases, in turn. Once a base is incorporated, the labeling group is removed, e.g., through the use of a photocleavable linking group, and where the label was not the terminating group, a terminator, upon the 3' end of the incorporated nucleotide, may be removed prior to subsequent interrogation.

As will be appreciated, prolonged interrogation of a limited population of reagents, e.g., fluorescent analogs and confined polymerase enzymes, can lead to photodamage of the various reagents and substantially impact the activity or functionality of the polymerase enzyme. In particular, it has been shown that prolonged illumination of DNA polymerases involved in synthesis using fluorescent nucleotide analogs results in a dramatic decrease in the enzyme's ability to synthesize DNA. Without being bound to any theory of operation, it is believed that the photodamage event affects the catalytic region of the enzyme, thus affecting either the ability of the enzyme to remain complexed with the template or its ability to process additional synthesis.

In accordance with the present invention, the above-described sequencing reaction may be carried out using dye-linker-nucleotide conjugates in which the linker incorporates a photoprotective agent, as described herein. In preferred aspects, the linker comprises both a reducing agent, such as DTT, MEA or BME, and an oxygen scavenger, such as GO-Cat.

Quencher-labeled fluorescent dyes of the invention (i.e., quenchers attached to dyes either directly or through a linker) may be useful in improving the photophysical properties of certain dyes, such as certain fluorescence lipophilic dye tracers. In addition, such compounds can be used to couple to not only nucleoside polyphosphates, but also to other molecules of interest.

Alternative Methods for Mitigation of Photodamage Impacts

In addition to the use of photoprotective agents, the present invention also provides alternative methods of mitigating the impact of photodamage on a reaction. Such alternative methods can be used in combination with the conjugates and methods described above to further alleviate the effects of species that can be generated during an illuminated reaction.

One alternative method of mitigating the impact of photodamage on the results of a given reaction is by only interrogating a reaction mixture, e.g., detecting fluorescent emission, during such portion of the illumination period before which excessive photodamage has occurred. This approach is particularly useful in the optical interrogation of reactions where components of the reaction that are susceptible to photodamage are spatially confined on an assay plate or substrate, either through the presence of structural confinements and/or through immobilization of the components. Examples of such confined reagents include surface immobilized or localized reagents, e.g., surface immobilized or associated enzymes, antibodies, etc. that are interrogated upon the surface, e.g., through fluorescence scanning microscopy or scanning confocal microscopy, total internal reflectance microscopy or fluorometry, surface imaging, or the like.

Another alternative method of mitigating the impact of photodamage on the results of a given reaction provides for the elimination of potentially damaging oxygen species using means other than the use of the photoprotective agents described above. In one example, dissolved oxygen species may be flushed out of aqueous systems by providing the reaction system under different gas environments, such as by exposing an aqueous reaction to neutral gas environments, such as argon, nitrogen, helium, xenon, or the like, to prevent dissolution of excess oxygen in the reaction mixture. By reducing the initial oxygen load of the system, it has been observed that photodamage effects, e.g., on polymerase mediated DNA synthesis, is markedly reduced. In particularly preferred aspects, the system is exposed to a xenon atmosphere. In particular, since xenon can be induced to form a dipole, it operates as a triplet state quencher in addition to supplanting oxygen in the aqueous system. (See, e.g., Vierstra and Poff, Plant Physiol. 1981 May; 67(5): 996-998) As such, xenon would also be categorized as a quencher, as set forth above.

These and further examples of alternative methods of mitigating photodamage which can be used in combination with methods and compositions of the invention described herein are provided in commonly owned U.S. patent application Ser. No. 11/201,768 filed Aug. 11, 2005, which is incorporated herein by reference in its entirety for all purposes and in particular for disclosure related to these methods of mitigating photodamage.

What is claimed is:

1. A method of performing an illuminated reaction comprising:
   (a) providing a substrate having a composition disposed thereon, wherein the composition comprises an enzyme and a nucleic acid template, the enzyme associated with a compound that comprises a nucleoside polyphosphate, a photoprotective agent, and a dye, wherein the nucleoside polyphosphate and the dye are connected through a linker comprising the photoprotective agent, and wherein the photoprotective agent is a member selected from the group consisting of: a triplet state quencher and a singlet oxygen quencher; and
   (b) processing the nucleic acid template with the enzyme while illuminating the composition on the substrate with an excitation illumination, wherein the compound prevents a loss of reactivity of the enzyme.

2. The method of claim 1, wherein the nucleoside polyphosphate is a member selected from the group consisting of: nucleoside triphosphate, nucleoside tetraphosphate, nucleoside pentaphosphate, and nucleoside hexaphosphate.

3. The method of claim 1, wherein the photoprotective agent is covalently bound to the dye or to the nucleoside polyphosphate.

4. The method of claim 1, wherein the photoprotective agent is covalently bound to the linker.

5. The method of claim 4, wherein the photoprotective agent is attached to a side group of the linker.

6. The method of claim 1, wherein the dye comprises a fluorescent labeling group.

7. A method of performing an illuminated reaction comprising:
   (a) providing a substrate having a composition disposed thereon, wherein the composition comprises an enzyme and a nucleic acid template, the enzyme associated with a compound that comprises a nucleoside polyphosphate, a photoprotective agent, and a dye, wherein the nucleoside polyphosphate and the dye are connected through a linker comprising the photoprotective agent; and
   (b) processing the nucleic acid template with the enzyme while illuminating the composition on the substrate with an excitation illumination, wherein the compound improves the ability of the enzyme to remain complexed with the nucleic acid template or the ability of the enzyme to further process the nucleic acid template as compared to when the compound is not present.

8. The method of claim 7, wherein the nucleoside polyphosphate is a member selected from the group consisting of: nucleoside triphosphate, nucleoside tetraphosphate, nucleoside pentaphosphate, and nucleoside hexaphosphate.

9. The method of claim 7, wherein the photoprotective agent is covalently bound to the dye or to the nucleoside polyphosphate.

10. The method of claim 9 wherein the photoprotective agent is covalently bound to the linker.

11. The method of claim 9, wherein the photoprotective agent is attached to a side group of the linker.

12. The method of claim 7, wherein the dye comprises a fluorescent labeling group.

13. The method of claim 7, wherein the photoprotective agent is a member selected from the group consisting of: a triplet state quencher and a singlet oxygen quencher.

14. The method of claim 1 wherein the linker is connected to the dye or the nucleoside phosphate through a peptide moiety.

15. The method of claim 1 wherein the linker comprises amino acids.

16. The method of claim 1 wherein the prevented loss of activity is greater than 10%.

17. The method of claim 1 wherein the prevented loss of activity is greater than 50%.

* * * * *